United States Patent
Veidung

(10) Patent No.: US 8,826,454 B2
(45) Date of Patent: Sep. 2, 2014

(54) METHOD FOR SECURE TRANSFER OF MEDICAL DATA TO A MOBILE UNIT/TERMINAL

(75) Inventor: Arne Veidung, Bønes (NO)

(73) Assignee: World Medical Center Holding SA, Rolle (CH)

( * ) Notice: Subject to any disclaimer, the term of this patent is extended or adjusted under 35 U.S.C. 154(b) by 1280 days.

(21) Appl. No.: 12/158,501

(22) PCT Filed: Dec. 21, 2006

(86) PCT No.: PCT/NO2006/000494
§ 371 (c)(1),
(2), (4) Date: Sep. 26, 2008

(87) PCT Pub. No.: WO2007/073208
PCT Pub. Date: Jun. 28, 2007

(65) Prior Publication Data
US 2009/0222898 A1    Sep. 3, 2009

(30) Foreign Application Priority Data

Dec. 22, 2005  (NO) .................................. 20056122

(51) Int. Cl.
G06F 12/16      (2006.01)
G06F 21/62      (2013.01)
G06F 19/00      (2011.01)

(52) U.S. Cl.
CPC .......... *G06F 21/6245* (2013.01); *G06F 19/324* (2013.01); *G06F 2221/2129* (2013.01); *G06F 19/323* (2013.01); *G06F 19/322* (2013.01); G06F 2221/2107 (2013.01)
USPC ............................................ 726/28; 715/265

(58) Field of Classification Search
CPC ......... G06F 21/10; G06F 21/12; G06F 21/30; G06F 21/6245; G06F 21/6272; G06F 19/20; G06F 19/32–19/326; G06F 21/00; G06F 21/60; G06F 21/602; G06F 21/62–21/6218; G06F 17/289; H04L 63/08; H04L 63/083

USPC .......... 726/7, 26–28, 2–5; 379/37–38, 88.19, 379/93.23, 100.01, 106.02, 142.03–142.06, 379/207.11, 207.13; 128/904; 715/264–265, 703; 704/8; 713/193, 713/189; 705/50–51

See application file for complete search history.

(56) References Cited

U.S. PATENT DOCUMENTS 6,082,776 A * 7/2000 Feinberg .......................... 283/72
6,161,082 A * 12/2000 Goldberg et al. ................. 704/3

(Continued)

FOREIGN PATENT DOCUMENTS

JP      06-314288     11/1994
JP      2002-251471   9/2002

(Continued)

OTHER PUBLICATIONS

Aziz et al. "Application of Mobile Phone in Medical Image Transmission" [Online], Jan. 14-15, 2003 [Retrieved on: May 30, 2014], 4th National conference on Telecommunication Technology Proceedings (NCTT 2003), pp. 80-83, Retrieved from: <http://ieeexplore.ieee.org/stamp/stamp.jsp?tp=&arnumber=1188307>.*

(Continued)

*Primary Examiner* — Saleh Najjar
*Assistant Examiner* — Eric W Shepperd
(74) *Attorney, Agent, or Firm* — Klarquist Sparkman, LLP

(57) ABSTRACT

Encoded medical data are made available to a mobile unit/terminal via a central server in a network. A request is sent to the central server; encoded medical data are generated in the server; encrypted data are transmitted from the server to the mobile unit/terminal, after authentication by a user; the encoded information is stored and protected in the mobile unit/terminal; upon authentication by a user, encoded information is sent to the server for decoding; and a picture containing user-readable text is sent to the mobile unit/terminal.

16 Claims, 1 Drawing Sheet

(56) References Cited

U.S. PATENT DOCUMENTS

| | | | |
|---|---|---|---|
| 6,302,844 B1* | 10/2001 | Walker et al. | 600/300 |
| 6,463,417 B1 | 10/2002 | Schoenberg | |
| 6,747,561 B1* | 6/2004 | Reeves | 340/573.1 |
| 6,868,494 B1 | 3/2005 | Shitara et al. | |
| 6,874,085 B1* | 3/2005 | Koo et al. | 713/165 |
| 6,970,827 B2 | 11/2005 | Zeltzer et al. | |
| 7,543,149 B2* | 6/2009 | Ricciardi et al. | 713/176 |
| 8,015,417 B2* | 9/2011 | Kato et al. | 713/193 |
| 8,140,854 B2* | 3/2012 | Ogawa | 713/183 |
| 2002/0010679 A1* | 1/2002 | Felsher | 705/51 |
| 2002/0016923 A1 | 2/2002 | Knaus et al. | |
| 2002/0035484 A1* | 3/2002 | McCormick | 705/2 |
| 2002/0083192 A1* | 6/2002 | Alisuag | 709/237 |
| 2002/0188466 A1 | 12/2002 | Barrette et al. | |
| 2002/0188472 A1* | 12/2002 | Fujisaka et al. | 705/2 |
| 2002/0194131 A1 | 12/2002 | Dick | |
| 2003/0037247 A1* | 2/2003 | Obara et al. | 713/193 |
| 2003/0040940 A1* | 2/2003 | Nehammer | 705/2 |
| 2003/0060808 A1* | 3/2003 | Wilk | 606/1 |
| 2003/0074564 A1* | 4/2003 | Peterson | 713/182 |
| 2004/0093239 A1 | 5/2004 | Ott et al. | |
| 2004/0162035 A1* | 8/2004 | Petersen et al. | 455/90.1 |
| 2004/0163123 A1* | 8/2004 | Okada et al. | 725/116 |
| 2005/0033369 A1* | 2/2005 | Badelt | 607/32 |
| 2005/0071632 A1* | 3/2005 | Pauker et al. | 713/165 |
| 2005/0076208 A1 | 4/2005 | Hori et al. | |
| 2005/0097052 A1* | 5/2005 | Systa et al. | 705/51 |
| 2005/0216311 A1* | 9/2005 | Gmelin et al. | 705/3 |
| 2005/0216313 A1 | 9/2005 | Claud et al. | |
| 2005/0250995 A1* | 11/2005 | Quy | 600/300 |
| 2006/0085347 A1* | 4/2006 | Yiachos | 705/51 |
| 2006/0106646 A1* | 5/2006 | Squilla et al. | 705/3 |
| 2006/0116902 A1* | 6/2006 | Amador et al. | 705/2 |
| 2006/0117314 A1* | 6/2006 | Sato | 717/174 |
| 2007/0143215 A1* | 6/2007 | Willems | 705/51 |
| 2009/0043253 A1* | 2/2009 | Podaima | 604/67 |
| 2010/0217663 A1* | 8/2010 | Ramer et al. | 705/14.42 |
| 2011/0276551 A1* | 11/2011 | Bessette | 707/705 |

FOREIGN PATENT DOCUMENTS

| | | |
|---|---|---|
| JP | 2003-242263 | 8/2003 |
| JP | 2005-018718 | 1/2005 |
| JP | 2005-115750 | 4/2005 |
| WO | WO0198866 A2 | 12/2001 |
| WO | WO02086791 A1 | 10/2002 |
| WO | WO 2005/057465 | 6/2005 |

OTHER PUBLICATIONS

International Search Report, May 11, 2007, 3 pages.

* cited by examiner

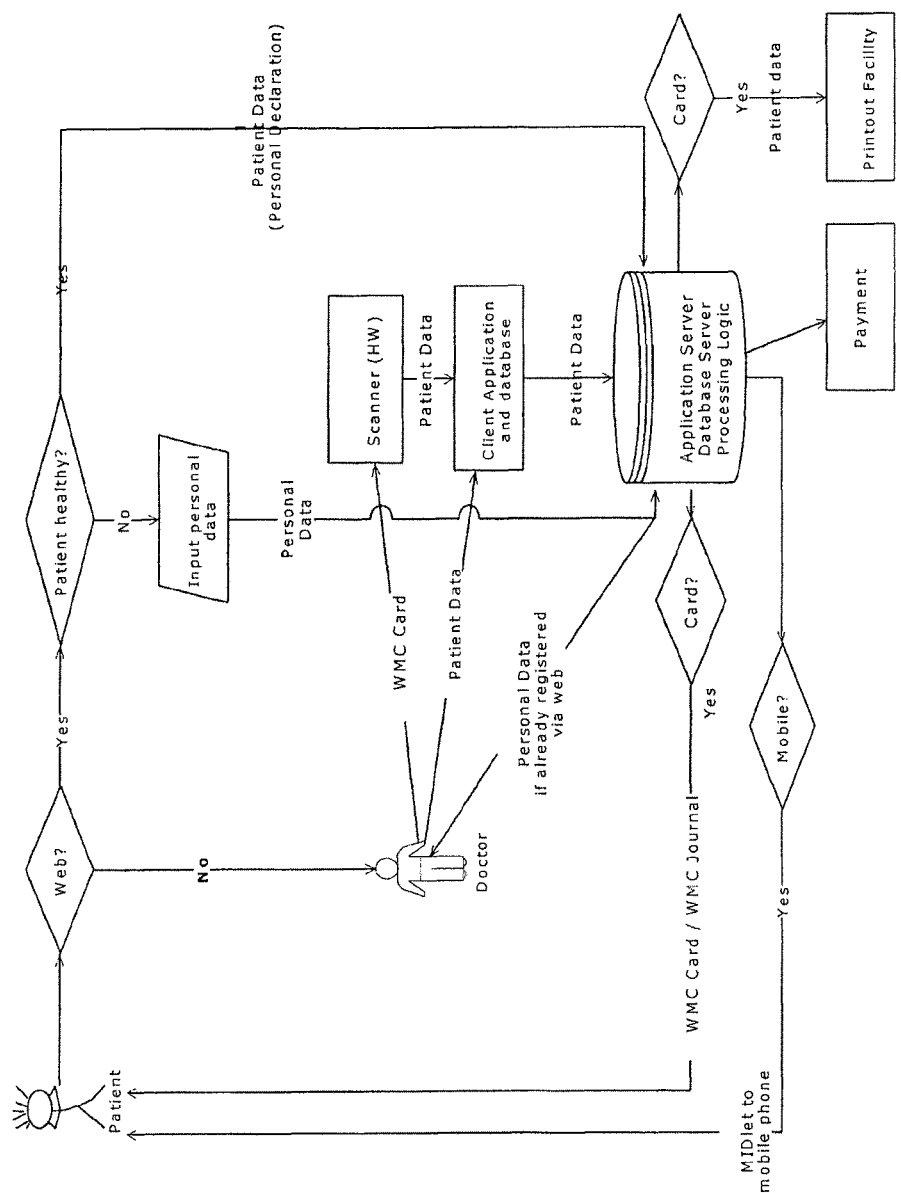

METHOD FOR SECURE TRANSFER OF MEDICAL DATA TO A MOBILE UNIT/TERMINAL

BACKGROUND AND SUMMARY

The present invention relates to a method for secure transfer of medical data to a mobile unit/terminal, where encoded medical data from a patient's doctor is made available via a central server in a network.

The described solution builds on a card that functions everywhere, wherever one has access to electricity, the interne or other technical equipment. The card can be kept together with credit cards and other ID cards. Health personnel will then be able to find the card as quickly as possible in case of an emergency. Health personnel can read the card either as standard text by breaking the seal, or electronically if they have access to a card reader. The card can therefore be read by doctors all over the world, regardless of whether they have an opportunity to scan it electronically or have access to other technical equipment.

The doctor will find all necessary medical info information written up according to the World Health Organization International Classification of Diseases (ICD-10) and World Health Organization Anatomical Therapeutic Chemical (ATC) classification. Any doctor familiar with World Health Organization classifications will therefore understand the information on the health card. To ensure that the data is kept securely, servers are preferably kept in locked, safe rooms. Preferred encrypting, such as Secured Socket Layer (SSL) encryption is used, in the transfer of all health related information, and all medical data that are sent to the server are stored in an encrypted format. All medical and pharmaceutical information which is sent to the server is preferably only stored while the health card is produced. As soon as the card is finished, the information can be permanently deleted. Personal information such as name and address is preferably stored so that one can later be able to make contact.

Briefly, NO 314,207 concerns a method for secure transfer of patient data on a data carrier, where the patient data are encoded and transferred via a network to a central server that encompasses a database, whereupon the data are stored in a storage unit in the server, that encoded data are transformed and written out on a data carrier that is kept by the patient, and that encoded data can be read from the data carrier with the help of a reader unit and be transformed to a readable format by a decoder. Said data carrier comprises a wafer that is carried by a user or which is fastened to a user's personal equipment, where the wafer comprises a two-dimensional code as an information carrier in encrypted format that is printed onto the wafer.

During the processing of NO 314.207, EP A1 423893 was mentioned among others. In said EP application a method is mentioned for storing and monitoring of patient related information at a health station, in which each patient is equipped with a patient connected electronic data carrier that can be read and reprogrammed. Patient data is stored in a central computer, both locally in the patient connected electronic data carrier and centrally in a central computer, where locally stored data for predetermined situations are compared with data that are centrally stored, and that the two types of data are harmonised if necessary.

Furthermore, DE A1 19840005 was highlighted, where a communication system is described with an input unit and an output unit, and also a memory storage unit for storage of patient data. The input unit is connected via an interface to terminals for bar code cards, patient circuit cards, and via another interface to the memory storage unit with the help of a communication terminal. The system is intended for use in hospitals and medical administration systems.

The present invention is consequently a further development of an international concept which, during medical treatment, places the safety of the patient in focus. With the system, a better diagnosis and basis for treatment are provided, and thereby also the correct medication wherever the patient is in the world. It is often a problem in emergency situations that the doctor in charge does not know anything about the medical history of the patient, the patient's use of medicines or allergies/reactions to medicines. This is particularly relevant when falling ill abroad.

Such vital information can be decisive to avoid the wrong treatment and the wrong medicine. This is a problem which is steadily on the increase and unfortunately may result in the death of patients.

One aspect of the present invention is consequently to make patient data even more accessible to the to a doctor who treats the patient. In addition, the system shall also be able to provide protection for the patient. Information will contain the diagnosis, illnesses/injuries, use of medication and allergies or reactions to medication of the patient.

Advantages with the system are that it can function as quality assurance for doctors or nurses in the daily treatment in an institution, at home visits or at ordinary visits by a doctor. If anything should happen, for example abroad, a person who needs treatment can contact a doctor, an emergency and accident facility or hospital, which is connected to the system. The information can thereafter be read and will thereby provide direct information about the medical data of the patient and the treatment can commence immediately.

In connection to the centrally placed database, a complete medication database can be arranged, which, for example, can demonstrate harmful interactions between different medicines. Thus, an automatic warning can be generated if a doctor tries to prescribe medicines that react with the other medicines a patient may take.

An object of the present invention is to provide a solution for the transfer of patient information, and which is part of the above mentioned system, to a mobile unit/terminal or the like.

The transfer of patient information can be accomplished by the following steps:
a) ordering transfer of encoded information to a mobile unit/terminal in that a request is sent to the central server,
b) generating encoded information containing medical data in the central server,
c) transfer transferring information in encrypted and encoded format from the server to the mobile unit/terminal after the user has authenticated himself,
d) storing and protecting the encoded information in the mobile unit/terminal,
e) transforming the encoded information to a readable format in that the user authenticates himself using a personal code that is sent from the mobile unit/terminal to the server, whereupon the ID is verified in the server, and that encoded information is sent to the server for decoding, and
f) transferring a picture containing user-readable text from the server to the mobile unit/terminal.

The user must preferably submit a password connected to his ID before encoded information is generated in step a). After encoded information is generated in step b), a notice can be sent to said user's mobile unit and/or e-mail address that medical data is available, and the user can reply to said notice and in step c) insert his ID and password for authentication.

After authentication has been approved by the server in step c), and encoded information is transferred to the mobile unit, the user can protect transferred data by putting in a personal code. To bring out the picture that is transferred to the mobile unit in step f), the user can preferably register correct ID and personal code.

The decoded information can also contain a programme code that can be used.

It is preferred that the encoding is based on the ICD-10 codes of the World Health Organization and the international code system for medicines ATC of the World Health Organization. For transfer of data, 128-bit SSL encryption is preferably used, and in this connection it is preferred to use telephones that comply with the Mobile Information Device Profile (MIDP) 2.0 specification for the use of software on embedded devices.

Ordering of encoded information to the mobile unit can be carried out in connection with ordering of a medical card.

BRIEF DESCRIPTION OF THE DRAWING

FIG. 1 shows a diagram of a system for a encoding and distributing medical information.

DETAILED DESCRIPTION

A system, sometimes referred to herein as "World Medical Centre" (WMC), comprises a central database which makes available patient data about any individual patient that is registered in the system. A patient's doctor will write the medical journal in his office. Central parts of the information in the journal are transferred, in encrypted foiinat, via a network to the central database and are entered on a structured medical card. The medical card will contain the patient's diagnosis, illnesses/injuries, use of medication and allergies or reactions to medicines. Before transfer, the data is automatically encrypted so that a person's privacy is protected.

The registered patient will receive a control copy of the data that are entered into the database for control against a copy that is received by the doctor. In addition, the patient can receive the medical card, normally also with a data carrier, which, for example can be a two-dimensional code that contains the same information. The code can be incorporated in a separate card or arranged to a self-adhesive means that, for example, can be stuck onto the back of a watch, piece of jewellery etc., and/or on a card to be stored together with other cards. The data carrier can also incorporate other types of code systems, such as, for example, bar codes, fluorised marks, digital chips, etc., which will be recognised by one skilled in the arts. The aim of the code is, among other things, that it must be possible to fix it to a separate object for simple storage.

In connection with the WMC system, there can also be arranged a complete medication database, which can, for example, show harmful interactions between different medicines. An automatic warning can thus be obtained if a doctor tries to prescribe medicines that react with the other medicines a patient may be on. Such an automatic warning can occur when the medication is entered into the card or database.

The code and the decoder are built up such that only those authorised can read the code. In a medical treatment, a scanner can be used in combination with a decoder so that others than the patient's regular doctor, i.e. authorised medical personnel, can read data on the wafer, or the card containing the same information.

After the treatment, the doctor can enter a completed treatment and medication in his database, whereupon the data are then transferred to the central database in WMC where they are registered. Data can thereafter be sent via the service centre to the patient's regular doctor. The database is updated automatically and a new card and new codes are sent to the patient if there are changes in relation to the journal. Correspondingly, the user must, if necessary, order new information to his mobile unit.

In the above mentioned process, the card carrier permits transfer of encrypted information to the production system of WMC. When the production is completed, medical information can be permanently deleted from the main system so that medical information is only stored with the card carrier in addition to his doctor.

A further development of the WMC system is that the users of the system shall be able to carry with them their own corresponding medical data in a mobile unit/terminal also, such as for example a mobile telephone, PDA or the like, or a portable computer. Meant in this connection with mobile unit is any mobile unit/terminal that can communicate over a network, even if in this description reference is in the main made to a mobile phone. The challenges in this connection are to make the transfer and reading of data as secure as possible.

The card carrier can order transfer of data to the mobile telephone/terminal. This is preferably made at the ordering of a card, but can also be made after a card has been issued or instead of a card. In this connection, the user must state a password connected to his ID. The user must accept the conditions that are associated with the ordering of medical data to the mobile phone. He/she must sign for this. In this context, it must be pointed out that with user is meant card carrier or doctor. Often, it will be natural that it is the doctor that orders transfer of information, and that it is the owner of the mobile unit card carrier which later must authenticate himself.

In the process with registration and ordering, there are, in the main, three set-ups (even if more are possible). Ordering and registering can be carried out via suitable web pages, or via a separate WMC client program;

1. The client fills in the journal together with the doctor. The doctor registers data and order. WMC registers and verifies medical data and order in the central server (application/database server). Data are transferred from server to production treatment and mobile service. WMC cards and journal are sent to the user and mobile unit. Thereafter, preferably all medical data are deleted from the server and production treatment.
2. The client fills in the journal together with the doctor. The journal is sent to WMC. WMC registers data and order, and verifies medical data in the central server (application/database server). Data are transferred from server to production treatment and mobile unit. WMC card and journal are sent to the user. Thereafter, all medical data are preferably deleted from the server and production treatment.
3. The client fills out a declaration, either a version that is written out or online on the internet. After consultation with the doctor, the declaration is sent to WMC. WMC registers, sorts and verifies medical data and order in the central server (application/database server). Data are transferred from server to production treatment and mobile unit. WMC card and journal are sent to the user. Thereafter, all medical data are preferably deleted from the server and production treatment.

When medical data are transferred centrally, a notice is sent to a user's mobile phone and/or a chosen e-mail address that the medical data are available, and for how long they are available. The time data are available to the card carrier/user is normally the same time, which is needed for the card production/production process. If a mobile telephone is used, the user can get information about a certain Wireless Application Protocol (WAP) address where the necessary program and data can be downloaded.

The card carrier, or user, must answer the message and, at the same time, state his ID and password for authentication. At accepted authentication, encrypted and decoded information is transferred to the mobile telephone as the card carrier has requested. The encoding is preferably based on the WHO's ICD-10 codes and the international code system for medicines ATC. In addition, names and telephone numbers of next of kin can be transferred and also a clear text field with is medical information that is not covered by ICD-10 or ATC codes. The transfer can be encrypted with 128-bit SSL encryption. The mobile unit owner protects the transferred data by putting in a personal pin code.

Data are stored in the mobile telephone in this format until the mobile unit owner has the need to have the encoded information translated to a readable language. In connection with storage of data on the mobile, it is normally required that a code is entered, for example, a four digit code that must be used, but this can be omitted if the operator permits it. The mobile unit owner can thereafter contact WMC via his mobile unit and authenticate himself via the personal pin code, whereupon the ID of the user is verified. With correct authentication it is permitted that the encoded information is transferred for decoding. Thereafter, a picture per language the mobile unit owner wants the codes decoded to is delivered/transferred back to the mobile telephone. SSL128 can be used in this process also.

When the pictures are transferred to the telephone, it will be possible to access these in that the telephone owner registers the correct ID and pin code. The user will then get several options in connection with viewing the data. A selection in the menu can lead the user to a choice of which language the information shall be shown in. Other choices can lead the user to program areas for deletion and/or addition of languages.

For security reasons, telephones that can use MIDP 2.0 are preferably used, as these telephones offer the possibility of encrypted communication from one end to the other. The invention is, of course, not limited to the use of such telephones, but can be used with all known mobile units/terminals that can handle encrypted information, or units/terminals that are developed in the future based on similar solutions.

The invention claimed is:

1. A method for secure transfer of medical data to a mobile phone, where encoded medical data from a doctor are made available via a central server in a network, the method comprising the following steps:
   receiving, by the central server, an order to transfer medical data to the mobile phone,
   generating, by the central server, encoded information containing encrypted medical data,
   after the generating of encoded information, sending, by the central server, a notice to the mobile phone to indicate that medical data are available,
   receiving, by the central server, a reply from the mobile phone, the reply containing a user ID and password for authentication,
   after receipt and authentication of the user ID and password, transmitting, by the central server, the encoded information containing the encrypted medical data to the mobile phone for storage and protection of the encoded information containing the encrypted medical data in the mobile phone,
   after verifying authentication information received by the central server from a user, receiving, at the central server the encoded information containing the encrypted medical data from the mobile phone,
   transforming, by the central server, the received encoded information containing the encrypted medical data to a picture displaying medical data in a readable format in a selected language, and
   transmitting, from the central server to the mobile phone, the picture for displaying as a digital image on a display screen of the mobile phone.

2. A method according to claim 1, wherein the central server must receive a password connected to a user's ID before encoded information is generated.

3. A method according to claim 1, wherein the transmitted encoded information also contains executable program code.

4. A method according to claim 1, wherein encoding is based on the World Health Organization's International Classification of Diseases (ICD-10) codes and the World Health Organization's Anatomical Therapeutic Chemical (ATC) classification.

5. A method according to claim 1, wherein 128-bit Secured Socket Layer (SSL) encryption is used for transfer of data.

6. A method according to claim 1, wherein the receiving of the order to transfer medical data to the mobile phone is carried out in connection with a receiving of an order for a medical card.

7. A method according to claim 1, wherein the transmitted encoded information and picture are suitable for use by a mobile phone that is enabled to use Mobile Information Device Profile (MIDP) 2.0.

8. A method for displaying medical data on a mobile phone, the method comprising the following steps:
   sending an order to a central server requesting that the central server transmit medical data, including data provided by a doctor, from the central server to a mobile phone,
   receiving, in the mobile phone, a notice from the central server that the medical data are available,
   sending, from the mobile phone, a reply to the notice, the reply containing an authorized user's ID and password for authentication,
   after sending the reply, receiving, by the mobile phone from the central server, encoded information containing an encryption of the medical data,
   storing and protecting the encoded information containing the encrypted medical data in the mobile phone,
   sending authentication information to the central server to request that the central server receive the encoded information containing the encrypted medical data from the mobile phone and transform the encoded information containing the encrypted medical data to a picture displaying medical data in a readable format in a selected language,
   upon receipt, by the mobile phone, of authorization by the central server, sending the encoded information containing the encrypted medical data from the mobile phone to the central server, and
   receiving, by the mobile phone, the picture from the central server, the picture displaying as a digital image on a display screen of the mobile phone.

9. A method according to claim 8, further comprising sending a correct password connected to an authorized user's ID to the central server to authorize the central server to transmit encoded information containing encrypted medical data to the mobile phone.

10. A method according to claim 8, further comprising, after the encoded information containing the encryption of the medical data are received in the mobile phone, protecting the received encoded information containing the encrypted medical data by inserting a personal code in the mobile phone.

11. A method according to claim 8, further comprising sending a correct user ID and personal code to the central server to authorize the central server to transmit the picture that is received in the mobile phone.

12. A method according to claim 8, wherein the encoded information that is received in the mobile phone also contains executable program code.

13. A method according to claim 8, wherein encoding is based on the World Health Organization's International Classification of Diseases (ICD-10) codes and the World Health Organization's Anatomical Therapeutic Chemical (ATC) classification.

14. A method according to claim, wherein 128-bit Secured Socket Layer (SSL) encryption is used for transfer of data.

15. A method according to claim 8, wherein the sending of an order to transfer medical data to a mobile phone is carried out in connection with sending an order for a medical card.

16. A method according to claim 8, wherein the mobile phone is enabled to use Mobile Information Device Profile (MIDP) 2.0.

* * * * *